(12) United States Patent
Yamazaki et al.

(10) Patent No.: US 6,736,807 B2
(45) Date of Patent: May 18, 2004

(54) LASER BEAM IRRADIATION PROBE

(75) Inventors: Iwao Yamazaki, Tokyo (JP); Yoshihiro Izawa, Tokyo (JP)

(73) Assignee: Ya-Man Ltd., Tokyo (JP)

( * ) Notice: Subject to any disclaimer, the term of this patent is extended or adjusted under 35 U.S.C. 154(b) by 70 days.

(21) Appl. No.: 10/148,168

(22) PCT Filed: Dec. 8, 2000

(86) PCT No.: PCT/JP00/08719

§ 371 (c)(1),
(2), (4) Date: May 31, 2002

(87) PCT Pub. No.: WO01/41872

PCT Pub. Date: Jun. 14, 2001

(65) Prior Publication Data

US 2002/0193779 A1 Dec. 19, 2002

(30) Foreign Application Priority Data

Dec. 8, 1999 (JP) ..................................... PH11-348587

(51) Int. Cl.[7] .............................................. A61B 18/20
(52) U.S. Cl. ............................................. 606/9; 607/89
(58) Field of Search ............................... 606/9; 607/88, 607/89

(56) References Cited

U.S. PATENT DOCUMENTS 5,259,380 A * 11/1993 Mendes et al. ................. 606/9
5,957,960 A * 9/1999 Chen et al. .................... 607/88
6,238,424 B1 * 5/2001 Thiberg .......................... 606/9
6,238,425 B1 * 5/2001 Thiberg .......................... 606/9
6,443,978 B1 * 9/2002 Zharov ......................... 607/91

FOREIGN PATENT DOCUMENTS

WO  WO 9415666 A1 * 7/1994 ............ A61N/1/00

* cited by examiner

Primary Examiner—Roy D. Gibson
Assistant Examiner—Henry M. Johnson
(74) Attorney, Agent, or Firm—Bacon & Thomas, PLLC; Felix J. D'Ambrosio

(57) ABSTRACT

The instrument of the present invention irradiates a relatively large skin area evenly with laser beams. A plurality of semiconductor laser diodes are arranged to form two lines with the semiconductor laser diodes of one line staggered with those of the other line, and the semiconductor laser diodes of each line are so inclined that their laser beams may focus on a single line. With this arrangement the plurality of laser beams provide a linear distribution of narrow beam, and the scanning area on the skin can be expanded accordingly. The beauty treatment on the skin or the depilation treatment can be expedited significantly. Advantageously the focusing points of the laser beams are distributed at an increased density, and the irradiation strength averages everywhere to attain the even beauty treatment.

2 Claims, 4 Drawing Sheets

LASER BEAM IRRADIATION PROBE

TECHNICAL FIELD

The present invention relates to an improvement in or relating to a laser beam irradiation instrument whose semiconductor lasers can project laser beams to one's skin to carry out beauty treatments for skin or depilation.

BACKGROUND ART

When one's skin is exposed to laser beams subsequent to depilation effected by means of depilatory, such laser beams are absorbed in the endoepidermal melanin so that a sufficient amount of heat may be generated to cause degeneration of protein in the skin tissue. As a result the sebaceous follicle and semi-spherical hair roots are so damaged that the follicular tissue may be hardened to suppress the growing of hair, thus causing a significant depilation effect.

When abnormal chromatophore cells scattered on the epiderm or corium of the skin such as spots and freckles are exposed to laser beams, such chromatophore cells are heated to disperse in the form of minute particles, which come up to the skin surface or are absorbed by vessels or lymphoducts as waste products. Thus, the normal skin revives.

In carrying out the beauty treatment for the skin with laser beams it is necessary to expose a relatively extensive skin area evenly to such laser beams; spots, freckles or downy hair are liable to appear in such a relatively extensive skin area.

Semiconductor lasers which are used in beauty treatments are very small in their irradiating areas, say several square microns ($\mu m^2$) to several tens square microns ($\mu m^2$), and unlike a He-Ne laser such semiconductor lasers cannot produce a fine, straight beam, but a fan-like beam diverging 30 to 45 degrees wide.

In the hope of increasing the energy density of laser beam at the beam-projection plane a condenser lens is used, and the beam diameter can be reduced to be equal to one to two millimeters at the focussing point.

SUMMARY OF THE INVENTION

To attain these objectives a laser beam irradiation instrument according to the present invention comprises: a plurality of semiconductor laser diodes arranged in two lines with the semiconductor laser diodes of one line staggered with those of the other line, the plurality of semiconductor laser diodes being so inclined that one plane in which the parallel optical axes of the semiconductor laser diodes of one line are contained may cross the other plane in which the parallel optical axes of the semiconductor laser diodes of the other line are contained; and a plurality of condenser lenses each arranged on the optical axis of each semiconductor laser, thereby causing each semiconductor laser to focus on the crossing line of the two planes.

Alternatively, a laser beam irradiation instrument according to the present invention comprises: a headed body whose front is recessed inward and defined by two oblique walls; a plurality of semiconductor laser diodes arranged in two lines on one oblique wall with the semiconductor laser diodes of one line staggered with those of the other line; another plurality of semiconductor laser diodes arranged in two lines on the other oblique wall with the semiconductor laser diodes of one line staggered with those of the other line; and a plurality of condenser lenses each arranged on the optical axis of each semiconductor laser, the semiconductor laser diodes on one oblique wall being so directed that one plane in which the parallel optical axes of the semiconductor laser diodes of one line are contained may cross the other plane in which the parallel optical axes of the semiconductor laser diodes of the other line are contained, thus defining one focussing line with the aid of the associated condenser lenses whereas the semiconductor laser diodes on the other oblique wall being so directed that one plane in which the parallel optical axes of the semiconductor laser diodes of one line are contained may cross the other plane in which the parallel optical axes of the semiconductor laser diodes of the other line are contained, thus defining the other focussing line with the aid of the associated condenser lenses, both focusing lines running parallel to each other.

In the hope of performing a beauty treatment on skin at an increased efficiency the inventor had the idea of arranging a plurality of laser beams in line rather than to converge to a single focussing point, so that the linear focussing of the laser beams may cover the irradiated area linearly or in one dimension. Then, the skin area can be swept by moving the laterally expanded laser beam longitudinally.

One objective of the present invention, therefore, is to make it possible to perform beauty treatments on the skin or depilation treatments at an increased efficiency.

Another objective of the present invention is to provide a linear laser beam having even strength of radiation, thereby permitting a required even treatment to be performed on the skin.

DISCLOSURE OF THE INVENTION

To attain these objectives a laser beam irradiation instrument according to claim 1 of the present invention comprises: a plurality of semiconductor laser diodes arranged in two lines with the semiconductor laser diodes of one line staggered with those of the other line, the plurality of semiconductor laser diodes being so inclined that one plane in which the parallel optical axes of the semiconductor laser diodes of one line are contained may cross the other plane in which the parallel optical axes of the semiconductor laser diodes of the other line are contained; and a plurality of condenser lenses each arranged on the optical axis of each semiconductor laser, thereby causing each semiconductor laser to focus on the crossing line of the two planes.

A laser beam irradiation instrument according to claim 2 of the present invention comprises: a headed body whose front is recessed inward and defined by two oblique walls; a plurality of semiconductor laser diodes arranged in two lines on one oblique wall with the semiconductor laser diodes of one line staggered with those of the other line; another plurality of semiconductor laser diodes arranged in two lines on the other oblique wall with the semiconductor laser diodes of one line staggered with those of the other line; and a plurality of condenser lenses each arranged on the optical axis of each semiconductor laser, the semiconductor laser diodes on one oblique wall being so directed that one plane in which the parallel optical axes of the semiconductor laser diodes of one line are contained may cross the other plane in which the parallel optical axes of the semiconductor laser diodes of the other line are contained, thus defining one focussing line with the aid of the associated condenser lenses whereas the semiconductor laser diodes on the other oblique wall being so directed that one plane in which the parallel optical axes of the semiconductor laser diodes of one line are contained may cross the other plane in which the parallel optical axes of the semiconductor laser diodes of the other line are contained, thus defining the other focussing line with the aid of the associated condenser lenses, both focusing lines running parallel to each other.

DETAILED DESCRIPTION OF THE PREFERRED EMBODIMENTS

Figure 1:
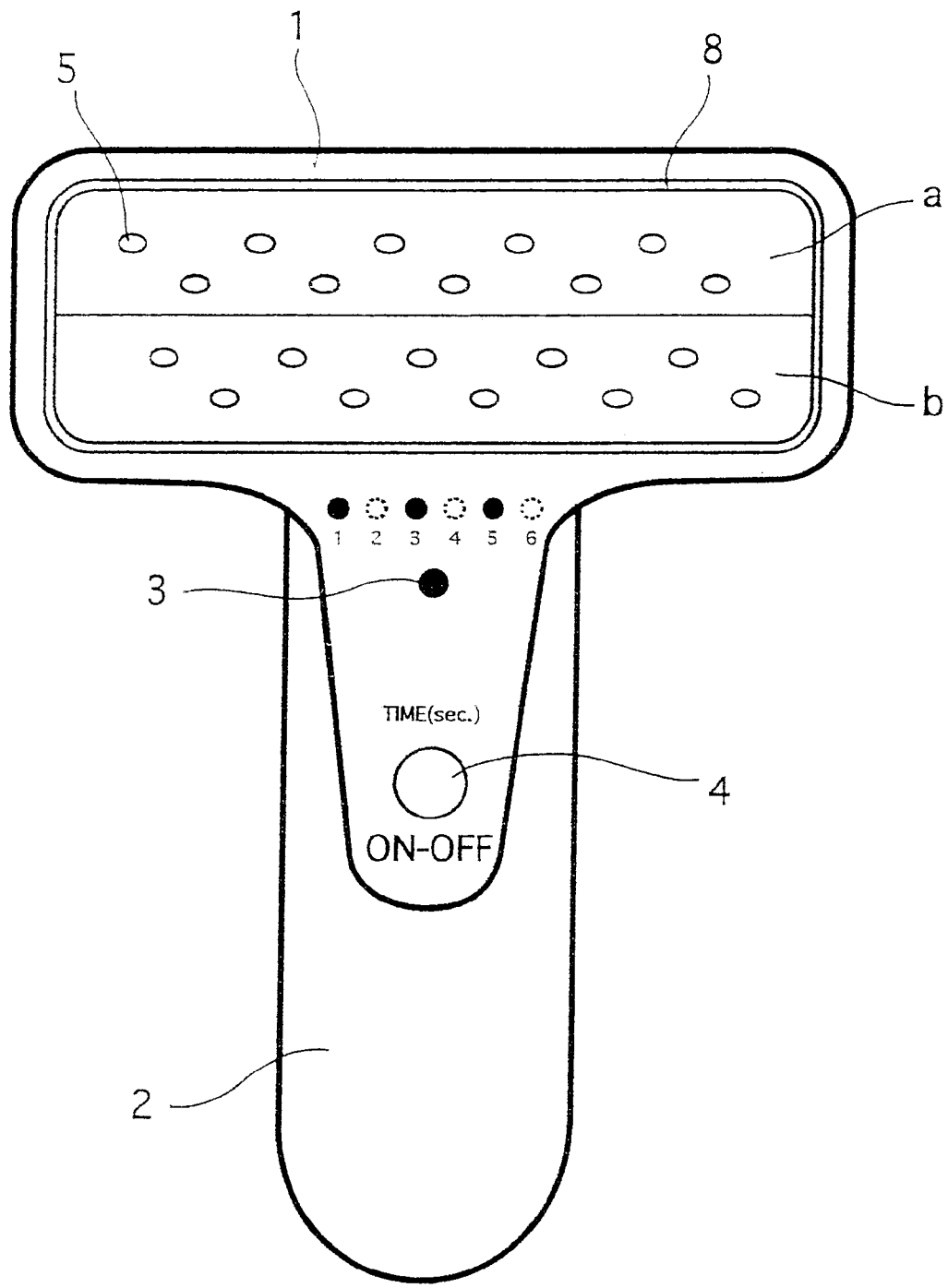
FIG. 1 is a front view of a laser beam irradiation instrument according to the present invention.
Figure 2:
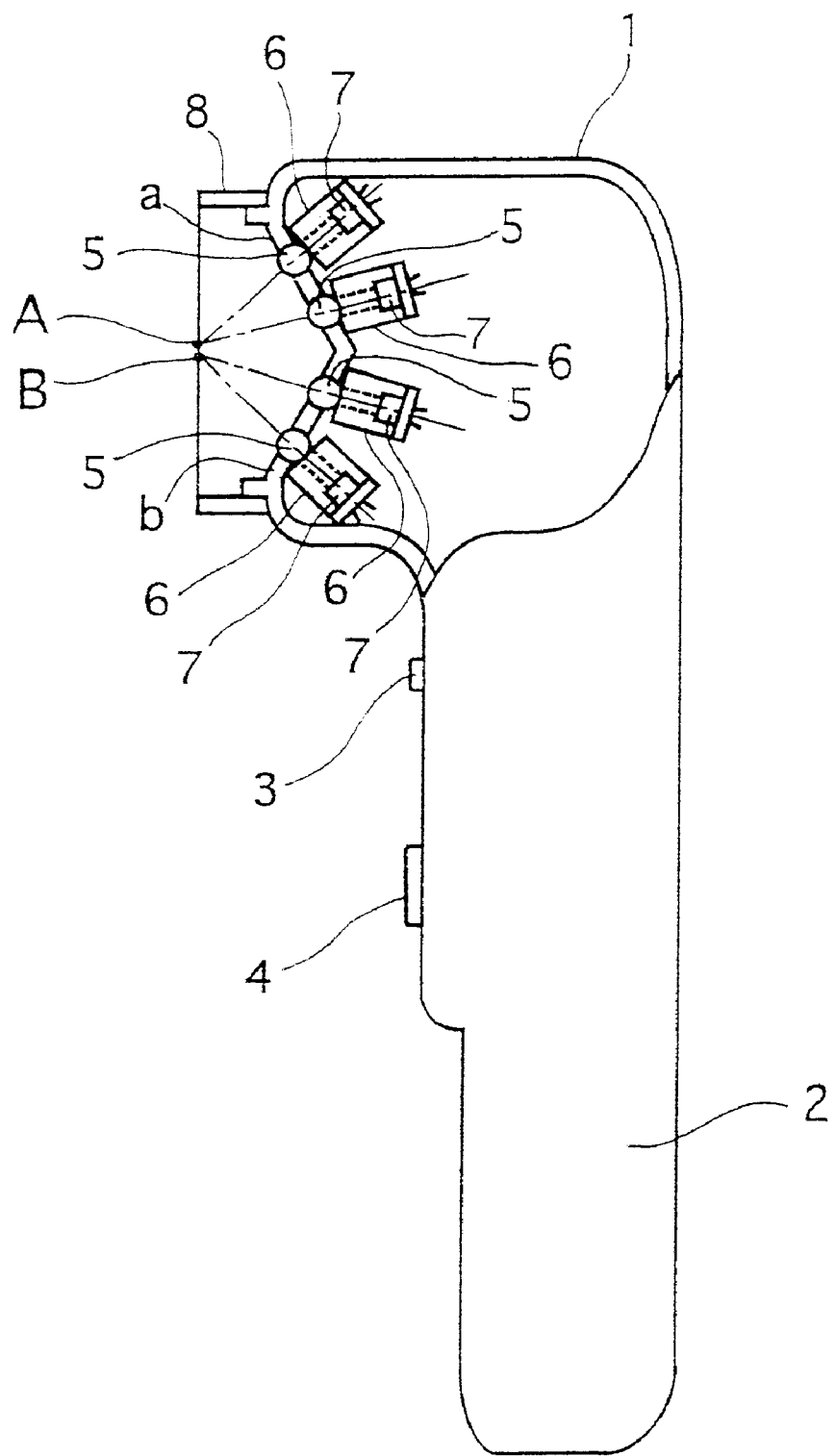
FIG. 2 is a side view of the laser beam irradiation instrument of FIG. 1, partly in section.
Figure 3:
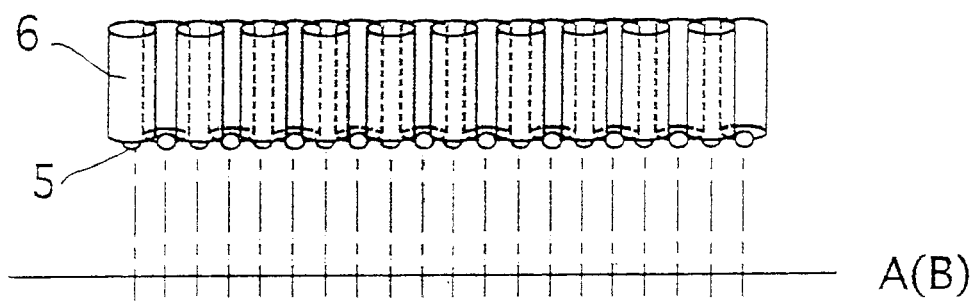
FIG. 3 illustrates how the semiconductor lasers are arranged in the laser beam irradiation instrument of FIG. 1.
Figure 4:
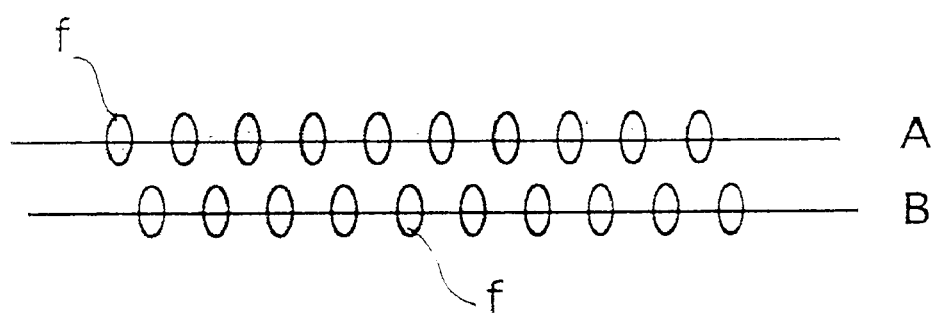
FIG. 4 illustrates how the focussing points are arranged.

Referring to FIGS. 1 and 2, a laser beam irradiation instrument according to one embodiment of the present invention comprises a "T"-shaped body comprising a lateral head 1 and a longitudinal grip 2 integrally connected to the lateral head 1, and a plurality of semiconductor laser diodes 7 (FIG. 2) arranged in two lines in each of the upper and lower halves of the front of the lateral head 1. The headed body 1 is equipped with an electric power supply (not shown) and a control (not shown) using a timer for permitting intermittent irradiation of laser beams at a given duty cycle. The grip 2 has an LED lamp 3 and a push button 4 both arranged on its front side.

The push button 4 when depressed makes the semiconductor laser diodes 7 turn on and off. Also, it permits selection of a desired working or "on" time among a plurality of predetermined irradiation lengths of time.

Specifically the first depression of the push button 4 will put the electric power supply in circuit with the control, thereby setting the irradiation of laser beams at one second, and at the same time, making the LED lamp 3 light green.

The subsequent or second depression of the push button 4 will set the irradiation of laser beams at two seconds, and at the same time, making the LED lamp 3 light green intermittently.

Sequential depression of the push button will make the irradiation of laser beams to be extended from three to six seconds, while making the LED lamp 3 light reddish yellow, reddish yellow intermittently, red and red intermittently in the order named.

Finally, the elongated (1.5 or more second-long) depression of the push button 4 will remove the electric power supply from the circuit, making everything turn off.

The grip is marked with icons and FIGS. 1 to 6 at a level higher than the LED lamp 3, thereby allowing the user to refer to such indications while depressing the push button 4 to realize how long the irradiation continues from the changing color and continuous or intermittent lighting condition of the LED lamp 3.

The one to six second-long irradiation of laser beams cannot cause any adverse effect on the skin.

As seen from FIG. 2, the headed body 1 has a "V"-shaped recess formed inward. Specifically the "V"-shaped recess is defined by two oblique walls "a" and "b", and each oblique wall has ten through holes made therein. A condenser lens 5 is press-fitted in each through hole. These condenser lenses 5 are arranged at regular intervals to form two lines on each oblique wall "a" or "b". The condenser lenses 5 of one line are staggered with those of the other line in each oblique wall. The number of the condenser lenses 5 and the "V" shaped recess should not be understood as being limitative; as many condenser lenses as required may be used, and a curved inward shape may be given to the front of the head 1.

Each spherical lens 5 has a heat sink 6 attached to its rear side, and a semiconductor laser 7 is fixed inside of the heat sink 6 with the optical axis of the semiconductor lens 7 aligned with the center axis of the heat sink 6.

As seen from FIG. 2, the semiconductor laser diodes 7 on the oblique wall "a" are so directed that one plane in which the parallel optical axes of the semiconductor laser diodes of one line are contained may cross the other plane in which the parallel optical axes of the semiconductor laser diodes 7 of the other line are contained, thus defining one focussing line A with the aid of the associated condenser lenses 5. Likewise, the semiconductor laser diodes 7 on the oblique wall "b" are so directed that they may focus on the focussing line B with the aid of the associated condenser lenses 5.

Both focusing lines A and B run parallel to each other. As seen from FIG. 4, the semiconductor laser diodes 7 are so arranged that the focussing points "f" on the focussing line A may be staggered with those on the focussing line B. Specifically the twenty semiconductor laser diodes 7 are so arranged in two lines that they may not be aligned with each other as viewed from the angle perpendicular to the lateral direction in which the ridge of the "V"-shaped recess is laid (see FIG. 1). The optical axes of the twenty semiconductor diodes 7 are separated at regular intervals as seen from FIG. 3.

Figure 5:
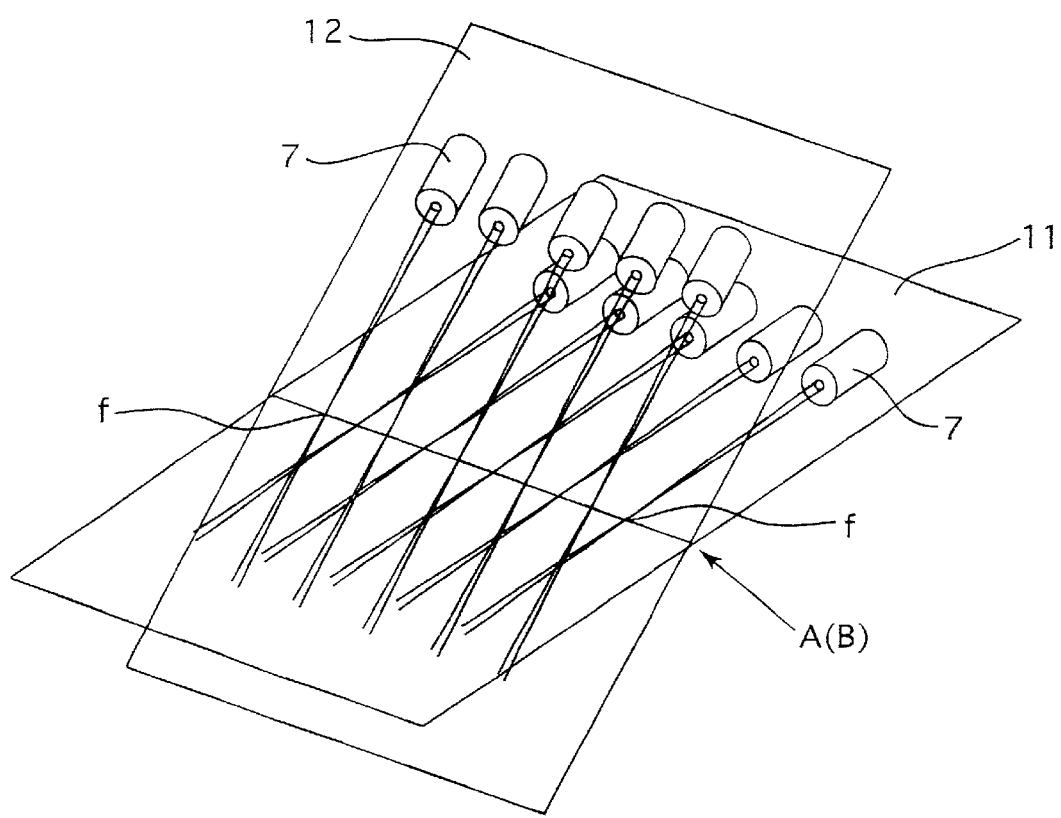
FIG. 5 is a perspective view of the arrangements of the semiconductor lasers in the laser beam irradiation instrument.

FIG. 5 illustrates how ten semiconductor diodes are arranged on each oblique wall. Specifically five semiconductor laser diodes 7 are arranged at regular intervals to form each of the two parallel lines with the semiconductor laser diodes of one line staggered with those of the other line. The five semiconductor laser diodes 7 have their optical axes running parallel on one optical plane 11 or 12. The optical planes 11 and 12 cross with each other to define the focussing line "A" or "B".

As seen from FIG. 5, the focussing points from the upper and lower lines of laser diodes are arranged alternately on the focussing lines "A" and "B".

Thus, the focusing points on the upper and lower lines on each oblique wall are staggered with each other, and all focussing points on the oblique walls of the "V"-shaped recess are arranged in staggering fashion.

The spherical lenses 5 permit the laser beams to focus at a relatively short distance, where all optical energy may be converged.

The optical energy thus converged is allowed to diverge a relatively wide range beyond the focussing line.

The so diverging optical energy is not strong enough to injure the skin even though such laser beams are thrown onto the skin. Thus, safety is assured.

In addition to the thermal effect the photo-electric, photo-magnetic, photo-dynamic, photo-chemical, photo-immunological, and photo-enzymatic effects can be caused, and as a consequence the photo-biophysical activation expedites the metabolism in the living body so that the flow of the blood may be accelerated. The laser beam is hardly absorbable in the water or blood, and therefore it can reach a significant depth under the skin.

The head 1 has a rectangular spacer 8 detachably attached to its circumference, thereby permitting the spherical lenses 5 to be a predetermined distance apart from the skin when applying the head 1 to the skin.

The spacer 8 is advantageously made of a transparent acryl, thereby permitting the laser beam-projected skin surface to be observed from the outside.

The spacer 8 may have a notch made on its circumference for ventilation.

In effecting a beauty treatment on the skin the push button 4 is depressed to turn the electric power supply "on". Then, the semiconductor laser diodes 7 turn "on" for one second, and "off" for one second alternately.

When it is desired that the length of irradiation time be changed, the push button 4 is depressed as many times as required to select a desired length of irradiation time among 1 to 6 second-long irradiation periods while keeping the extinction period at one second irrespective of how long the irradiation of laser beams may continue.

As may be understood from the above, a laser beam irradiation instrument according to the present invention has its semiconductor laser diodes so arranged as to permit their laser beams to focus on line at very short intervals, thereby producing an apparently linear expansion of laser beam. Longitudinal movement of the laser beam irradiation instrument on the skin causes such an apparently linear expansion of laser beam to scan the skin effectively for beauty treatment.

After the semiconductor laser diodes 7 turn on, the open end of the spacer 8 is applied to a selected skin area to be treated, and the head 1 is moved slowly in the longitudinal direction.

Many laser beam spots are thrown onto the selected skin area to spread laterally, and the lateral extension of laser beam are moved longitudinally to scan the selected skin area. Thus, the selected skin area is exposed evenly to the laser beam.

The laser beam is selectively responsive to abnormal chromatophores such as melanin. Thanks to the chromatophore selectivity of the laser beam surrounding normal cells cannot be adversely affected even though the laser beam is allowed to disperse under the skin.

The lateral, parallel-arranged lines A and B of focusing points "f" have their focusing points "f" of one of two adjacent parallel lines staggered with those of the other line. Thanks to this unique arrangement of focussing points, longitudinal movement of the head permits the lateral lines of focussing points to scan the selected skin area evenly at an increased efficiency without leaving any unexposed portion behind.

Industrial Applicability

As may be understood from the above, a laser beam irradiation instrument according to the present invention has its semiconductor laser diodes so arranged as to permit their laser beams to focus on line at very short intervals, thereby producing an apparently linear expansion of laser beam. Longitudinal movement of the laser beam irradiation instrument on the skin causes such an apparently linear expansion of laser beam to scan the skin effectively for beauty treatment.

What is claimed is:

1. A laser beam irradiation instrument, comprising:
a plurality of semiconductor laser diodes arranged in two lines, with the semiconductor laser diodes of one line staggered with respect to those of the other line, wherein said plurality of semiconductor laser diodes in each line defining a plurality of parallel optical axes which in turn define a plane of the semiconductor laser diodes, and said planes cross each other and define a crossing line; and
a plurality of condenser lenses each arranged on a respective optical axis of said semiconductor laser diodes, thereby causing each semiconductor laser to focus on the crossing line of the two planes.

2. A laser beam irradiation instrument, comprising:
a headed body having a front which is recessed inward and defines two oblique walls;
a plurality of semiconductor laser diodes arranged in two lines on one of said oblique walls, with the semiconductor laser diodes of one line staggered with respect to those of the other line, wherein said plurality of semiconductor laser diodes in each line defining a plurality of optical axes which in turn define a plane of the semiconductor laser diodes;
a plurality of semiconductor laser diodes arranged in two lines on the other of said oblique walls, with the semiconductor laser diodes of one line staggered with respect to those of the other line, wherein said plurality of semiconductor laser diodes in each line defining a plurality of optical axes which in turn define a plane of the semiconductor laser diodes; and
a plurality of condenser lenses each arranged on a respective optical axis of said semiconductor laser diodes, wherein:
said semiconductor laser diodes on one of said oblique walls being so directed that one of said planes in which said parallel optical axes of said semiconductor laser diodes of one line cross the other of said planes in which said parallel optical axes of said semiconductor laser diodes of the other line, thus defining one focusing line with the aid of said associated condenser lenses;
said semiconductor laser diodes on the other of said oblique walls being so directed that one of said planes in which said parallel optical axes of said semiconductor laser diodes of one line cross the other of said planes in which said parallel optical axes of said semiconductor laser diodes of the other line, thus defining another focusing line with the aid of said associated condenser lenses; and
both of said focusing lines running parallel to each other.

* * * * *